United States Patent [19]

Perronnet et al.

[11] 4,170,465
[45] Oct. 9, 1979

[54] NOVEL CROTONAMIDES

[75] Inventors: Jacques Perronnet; Pierre Girault, both of Paris, France

[73] Assignee: Roussel UCLAF, Paris, France

[21] Appl. No.: 568,383

[22] Filed: Apr. 16, 1975

[30] Foreign Application Priority Data

Apr. 22, 1974 [FR] France ............................ 74 13891

[51] Int. Cl.² ...................... A01N 9/20; C07C 103/60
[52] U.S. Cl. ........................................ 71/118; 11/106; 260/561 N
[58] Field of Search ...................... 71/118; 260/561 N

[56] References Cited

U.S. PATENT DOCUMENTS

| 2,744,817 | 5/1956 | Toornman | 71/118 |
|---|---|---|---|
| 3,278,597 | 10/1966 | Neighbors | 71/118 |
| 3,291,592 | 12/1966 | Evans | 71/92 |
| 3,574,748 | 4/1971 | Mayer et al. | 260/561 N |
| 3,657,340 | 4/1972 | Johnson et al. | 71/118 |
| 3,703,518 | 11/1972 | Inoi et al. | 260/561 N |
| 3,860,603 | 1/1975 | Imamura et al. | 260/561 N |

FOREIGN PATENT DOCUMENTS 7313245 3/1974 Netherlands ............................ 71/118

1137466 12/1968 United Kingdom ...................... 71/118

OTHER PUBLICATIONS

Byrnes et al., "Vinyl Ether Hydrolysis II General, etc.", (1971), JACS 94, pp. 7016–7019, (1972).

*Primary Examiner*—Glennon H. Hollrah
*Attorney, Agent, or Firm*—Hammond & Littell

[57] ABSTRACT

Novel crotonamides of the formula

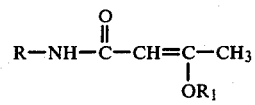

wherein R is selected from the group consisting of adamantyl, bornyl, 5',6'-dihydroendo-5'-dicyclopentadienyl and saturated and unsaturated cycloalkyl of 3 to 8 carbon atoms optionally substituted with a member of the group consisting of alkyl of 1 to 6 carbon atoms, hydroxy, chlorine and alkoxycarbonyl of 1 to 6 alkyl carbon atoms and $R_1$ is alkyl of 1 to 3 carbon atoms having pre- and post-emergence herbicidal properties.

18 Claims, No Drawings

NOVEL CROTONAMIDES

STATE OF THE ART

Our copending, commonly assigned U.S. patent application Ser. No. 398,415 filed Sept. 18, 1973, now abandoned describes various croton anilides occuring in their E or Z isomer forms or mixtures thereof as herbicides.

OBJECTS OF THE INVENTION

It is an object of the invention to provide the novel crotonamides of formula I and to provide novel intermediates therefor.

It is another object of the invention to provide a novel process for the preparation of the crotonamides of formula I.

It is a further object of the invention to provide novel herbicidal compositions and to provide a novel method of killing weeds.

These and other objects and advantages of the invention will become obvious from the following detailed description.

THE INVENTION

The novel crotonamides of the invention have the formula

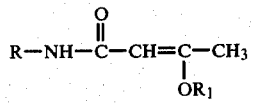

wherein R is selected from the group consisting of adamantyl, bornyl, 5',6'-dihydroendo-5'-dicyclopentadienyl and saturated and unsaturated cycloalkyl of 3 to 8 carbon atoms optionally substituted with a member of the group consisting of alkyl of 1 to 6 carbon atoms, hydroxy, chlorine and alkoxycarbonyl of 1 to 6 alkyl carbon atoms and $R_1$ is alkyl of 1 to 3 carbon atoms. The compounds can exist in the form of their E isomer or Z isomer or mixtures thereof.

When R is cycloalkyl, examples of suitable cycloalkyl groups are cyclopropyl, cyclobutyl, cyclopentyl, cyclohexyl, cyclohexenyl, cycloheptyl and cyclooctyl optionally substituted with alkyl such as methyl, ethyl, propyl, butyl, hydroxy, chlorine or alkoxycarbonyl. $R_1$ may be alkyl such as ethyl, methyl and propyl.

The novel process of the invention for the preparation of the crotonamides of formula I comprises reacting a compound of the formula

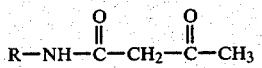

where R has the above definition with a lower alkyl orthoformate having 1 to 3 alkyl carbon atoms in the presence of an acid agent. The reaction occurs in two steps with the first step of acetalization leading to a product of the formula

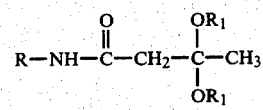

which spontaneously or upon heating transforms into the compound of formula I. The acid agent may be p-toluene sulfonic acid, hydrochloric acid, sulfuric acid or ion exchange resins in the acid form.

The starting acetylacetamides of formula II may be prepared by reacting diketene with the appropriate amine.

The novel herbicidal compositions of the invention are comprised of an herbicidally effective amount of at least one compound of formula I and a carrier. The compositions may also contain additional pesticidal agents or other products which influence the growth of plants. The compositions may be in the form of powders, granules, suspensions, emulsions or solutions which may contain besides the active products anionic, cationic or non-ionic surface active agents, inert powders such as clays, talc, silicates or kieselguhr and a vehicle such as water, alcohol, hydrocarbons or other organic solvents or a mineral, animal or vegetable oil. The herbicidal compositions preferably contain 10 to 80% of the active compound of formula I.

The novel method of the invention of killing weeds comprises contacting the weeds with a herbicidally effective amount of at least one compound of formula I. The compounds may be applied either pre-emgergence or post-emergence and the usual useful application rate is 0.625 to 5.0 Kg/ha. Tests have shown the method to be effective against diverse plant species in different botanical families.

In the following examples there are described several preferred embodiments to illustrate the invention. However, it should be understood that the invention is not intended to be limited to the specific embodiments.

EXAMPLE 1

N-cyclohexyl-3-methoxy-crotonamide

STEP A: N-cyclohexyl-3,3-dimethoxy-butyramide

A mixture of 500 ml of benzene and 99 g of cyclohexyl amine were introduced over 30 minutes to 84 g of diketene and after stirring for 4 hours at 20° C., the mixture was evaporated to dryness by distillation under reduced pressure. The residue was taken up in isopropyl ether and the solution was cooled and vacuum filtered. The recovered precipitate was dried and crystallized from isopropyl ether to obtain 137 g of N-cyclohexyl-acetylacetamide melting at 74° C.

A mixture of 36.6 g of N-cyclohexyl-acetylacetamide, 32 g of methyl orthoformate, 100 ml of methanol and 1 g of p-toluene sulfonic acid was stirred for 4 hours at 25° C. and after the addition of 2 g of quinoline, the mixture was evaporated to dryness under reduced pressure. The residue was added to isopropyl ether and the mixture was cooled and vacuum filtered. The recovered precipitate was dried to obtain 40 g of N-cyclohexyl-3,3-dimethoxy-butyramide melting at 66° C.

STEP B: N-cyclohexyl-3-methoxy-crotonamide

A mixture of 40 g of N-cyclohexyl-3,3-dimethoxy-butyramide in 200 ml of toluene was stirred and heated to 145° C. to distill an azeotrope of toluene and methanol. After 3 hours, the mixture was cooled and evaporated to dryness under reduced pressure. The oil residue was chromatographed over silica gel and was eluted with a 7-3 methylene chlorideethyl acetate mixture. The fractions with an Rf of 0.55 were recovered and were concentrated to dryness under reduced pressure. The residue was added to isopropyl ether which was iced and vacuum filtered. The recovered precipitate was dried to obtain 18 g of N-cyclohexyl-3-methoxy-crotonamide melting at 109° C.

Analysis: $C_{11}H_{19}NO_2$; molecular weight=197.268 Calculated: %C. 66.98; %H. 9.71; %N. 7.1; Found: 67.3; 9.9; 7.2.

The RMN spectra showed the compound to be the E isomer.

EXAMPLE 2

N-(3'-cyclohexenyl)-3-methoxy-crotonamide 13.6 ml of diketene were added over 20 minutes to a mixture of 17.4 g of 3-amino-cyclohexene in 174 ml of benzene and after stirring the resulting mixture at room temperature for 5 hours, the mixture was distilled to dryness under reduced pressure to obtain 28.8 g of N-(3'-cyclohexenyl)acetylacetamide melting at 50° C.

25 g of N-(3'-cyclohexenyl)-acetylacetamide and 0.3 g of p-toluene sulfonic acid were added to a mixture of 50 ml of methanol and 25 g of ethyl orthoformate and the resulting solution was allowed to stand at 20° C. for 3 days. 0.6 ml of quinoline were added thereto and the mixture was distilled to dryness under reduced pressure. The oil residue was dissolved in toluene and the solution was stirred at 145° C. for 5 hours while distilling of a toluene-methanol azeotrope. The mixture was then evaporated to dryness under reduced pressure and the residue was added to isopropyl ether. The mixture was iced and vacuum filtered and the recovered precipitate was dried to obtain 15.8 g of N-(3'-cyclohexenyl)-3-methoxy-crotonamide melting at 112° C.

Analysis: $C_{11}H_{17}NO_2$: molecular weight=195.265 Calculated: %C. 67.66; %H. 8.78; %N. 7.18; Found: 67.9; 9.1; 7.1.

The RMN spectra showed the product to be the E isomer.

EXAMPLE 3

N-(cyclooctyl)-3-methoxy-crotonamide 84 g of diketene were added over 30 minutes to a stirred mixture of 127 g of cyclooctylamine and 800 ml of tetrahydrofuran cooled to −5° C. and the mixture was stirred for 4 hours at 20° C. and then evaporated to dryness under reduced pressure to obtain 210 g of N-cyclooctyl-acetylacetamide melting at 44° C. 63 g of the said product and 1 g of p-toluene sulfonic acid were added to a mixture of 150 ml of methanol and 40 g of methyl orthoformate and after stirring the mixture for 16 hours, 1.5 ml of quinoline were added thereto. The mixture was distilled to dryness under reduced pressure and the residual oil was dissolved in toluene. The solution was heated at 145° C. for 4 hours while distilling off a methanol-toluene azeotrope. The mixture was distilled to dryness under reduced pressure and the oil residue was chromatographed over silica gel. An 8-2 methylene chloride-acetone mixture was used as the eluant and the product was empasted with isopropyl ether to obtain 45 g of N-cyclooctyl-3-methoxy-crotonamide melting at 116° C.

Analysis: $C_{13}H_{23}NO_2$; molecular weight=225.318 Calculated: %C. 69.29; %H. 10.29; %N. 6.22; Found: 69.4; 10.1; 6.2.

The RMN spectra showed the product to be the E isomer.

EXAMPLE 4

N-(1'-adamantyl)-3-methoxy-crotonamide 19 g of 1-amino-adamantane were added to 200 ml of benzene and then 9.5 ml of diketene were added thereto over 10 minutes. The mixture was stirred for 2½ hours at room temperature and after the addition of activated charcoal, the mixture was stirred and filtered. The filtrate was distilled to dryness under reduced pressure and the residue was added to isopropyl ether. The mixture was vacuum filtered to obtain 23.6 g of N-(1-adamantyl)-acetylacetamide melting at 80° C. 23.5 g of the said product and 1 g of p-toluene sulfonic acid were added to a mixture of 50 ml of methanol and 15 ml of methyl orthoformate and the mixture was stirred at room temperature for 24 hours and was then cooled. 2 ml of quinoline were added and the mixture was vacuum filtered. The precipitate was dried to obtain 25.1 g of N-(1-adamantyl)-3,3-dimethoxy-butyramide melting at 140° C.

23.5 g of the latter product in 235 ml of toluene was refluxed for 3 hours while distilling a toluene-methanol azeotrope and was then cooled and vacuum filtered. The precipitate was dried to obtain 17 g of N-(1'-adamantyl)-3-methoxy-crotonamide melting at 202° C.

Analysis: $C_{15}H_{23}NO_2$; molecular weight=249.338 Calculated: %C 72.26; %H 9.30; %N 5.62; Found: 72.5; 9.50; 5.6.

The RMN spectra showed the product to be the E isomer.

EXAMPLE 5

N-cycloheptyl-3-methoxy-crotonamide 37.1 g of diketene were added with stirring over 15 minutes to a mixture of 50 g of cycloheptylamine and 600 ml of tetrahydrofuran cooled to 6° C. and the mixture was stirred for 4 hours at room temperature. The mixture was distilled to dryness under reduced pressure and the residue was chromatographed over silica gel with elution with an 8-2 methylene chloride-acetone mixture to obtain 60 g of N-cycloheptyl-acetylacetamide melting at 52° C. 40 g of the said product and 1 g of p-toluene sulfonic acid were added to a mixture of 32 g of methyl orthoformate and 100 ml of methanol and after stirring the mixture for 8 hours at room temperature, 2 ml of quinoline were added thereto. The mixture was distilled to dryness under reduced pressure and the residue was added to toluene. The mixture was heated at 145° C. for 4 hours while distilling a toluene-methanol azeotrope. The toluene was evaporated by distillation under reduced pressure and the residue was chromatographed over silica gel. An 8-2 methylene chloride-methanol mixture was the eluant and the product was empasted with isopropyl ether to obtain 22 g of N-cycloheptyl-3-methoxy-crotonamide melting at 120° C. The RMN spectra showed the product to be the E isomer.

Analysis: $C_{12}H_{21}NO_2$; molecular weight=211.298 Calculated: %C. 68.20; %H. 10.02; %N. 6.63; Found: 68.4; 10.3; 6.9.

EXAMPLE 6

N-(5',6'-dihydro-endo-5'-dicyclopentadienyl)-3-methoxy-crotonamide

A solution of 6.75 g of diketene in 20 ml of tetrahydrofuran was added with stirring to a mixture of 12 g of exo-5-amino-5,6-dihydro-endo-dicyclopentadiene in 60 ml of tetrahydrofuran and the mixture was stirred for 4 hours at 20° C. and evaporated to dryness under reduced pressure. The residue was chromatographed over silica gel and was eluted with an 8-2 methylene chloride-acetone mixture to obtain 13 g of N-(5,6-dihydro-endo-5-dicyclopentadienyl)-acetylacetamide. 12 g of the said product, 8 g of methyl orthoformate and 1 g of p-toluene sulfonic acid were added to 10 ml of methanol and the mixture was allowed to stand for 24 hours. 0.6 ml of quinoline were added thereto and the mixture was evaporated to dryness under reduced pressure. The residue was added to toluene and the mixture was stirred and heated at 145° C. for 3 hours while distilling a toluene-methanol azeotrope. The mixture was evaporated to dryness under reduced pressure and the residue was chromatographed over silica gel. Elution with an 8-2 methylene chloride-methanol mixture gave 7 g of N-(5',6'-dihydro-endo-5'-dicyclopentadienyl)-3-methoxy-crotonamide melting at 145° C. The RMN spectra showed that the product was the E isomer.

Analysis: $C_{15}H_{21}NO_2$; molecular weight=247.346 Calculated: %C. 72.84; %H. 8.56; %N. 5.66; Found: 73.0; 8.5; 5.6.

EXAMPLE 7

N-(4'-methylcyclohexyl)-3-methoxy-crotonamide 29 g of diketene were added over 20 minutes to a stirred mixture of 39 g of 4-methylcyclohexylamine in 100 ml of tetrahydrofuran and the mixture was stirred at 20° C. for 3 hours. Isopropyl ether was added thereto and the precipitate formed was recovered by vacuum filtration, was washed and dried to obtain 46 g of N-(4-methylcyclohexyl)-acetylacetamide melting at 111° C. A mixture of 46 g of the latter product, 37 g of methyl orthoformate, 1.5 g of p-toluene sulfonic acid and 100 ml of methanol was stirred for 2 hours at 20° C. and after standing for 16 hours, 3 ml of quinoline were added thereto. The mixture was distilled to dryness under reduced pressure and the residue was added to toluene. The stirred mixture was heated at 145° C. for 3 hours while distilling a toluene-methanol azeotrope and was then cooled and evaporated to dryness under reduced pressure. The residue was chromatographed over silica gel and elution with an 8-2 methylene chloride-acetone mixture gave 24 g of N-(4'-methylcyclohexyl)-3-methoxy-crotonamide melting at 125° C. The RMN spectra showed the product to be the E isomer.

Analysis: $C_{12}H_{21}NO_2$; molecular weight=211.298 Calculated: %C. 68.21; %H. 10.02; %N. 6.62; Found: 68.3; 10.1; 6.5.

EXAMPLE 8

N-(1'-methylcyclohexyl)-3-methoxy-crotonamide

A solution of 13.5 g of diketene in 50 ml of tetrahydrofuran was added to a mixture of 18 g of 1-methylcyclohexylamine and 180 ml of tetrahydrofuran and the mixture was stirred at 10° C. for 4 hours. The mixture was evaporated to dryness under reduced pressure and the residue was chromatographed over silica gel. Elution with an 8-2 methylene chloride-acetone mixture gave 28 g of N-(1-methylcyclohexyl)acetylacetamide with a refractive index of $N_D^{23}=1.4865$. 6 g of the latter product and 0.2 g of p-toluene sulfonic acid were added to a mixture of 5 g of methyl orthoformate and 10 ml of methanol. The mixture was stirred and allowed to stand for 16 hours at 20° C. 6.5 ml of quinoline were added and the mixture was evaporated to dryness under reduced pressure. The residue was added to toluene and the mixture was heated at 145° C. for 3 hours while distilling a toluene-methanol azeotrope. The mixture was evaporated to dryness under reduced pressure and the residue was chromatographed over silica gel. Elution with an 8-2 methylene chloride-acetone mixture gave 4 g of N-(1'-methylcyclohexyl)-3-methoxy-crotonamide melting at 105° C. The RMN spectra showed the product to be the E isomer.

Analysis: $C_{12}H_{21}NO_2$; molecular weight=211.298 Calculated: %C. 68.21; %H. 10.02; %N. 6.62; Found: 68.5; 9.9; 6.4.

EXAMPLE 9

N-(3'-methylcyclohexyl)-3-methoxy-crotonamide

A solution of 7.5 g of diketene in 30 ml of tetrahydrofuran was added to a mixture of 10 g of 3-methylcyclohexylamine and 60 ml of tetrahydrofuran and the mixture was stirred at 20° C. for 4 hours and evaporated to dryness under reduced pressure. The residue was chromatographed over silica gel and was eluted with an 8-2 methylene chloride-acetone mixture to obtain 12 g of N-(3-methylcyclohexyl)-acetylacetamide. 12 g of the latter product and 0.3 g of p-toluene sulfonic acid were added to a mixture of 10.6 g of methyl orthoformate and 20 ml of methanol and the mixture was stirred at 20° C. for 1 hour and stood still for 16 hours at 20° C. 0.6 g of quinoline were added thereto and the mixture was evaporated to dryness under reduced pressure. The residue was added to 50 ml of toluene and the mixture was heated at 145° C. for 3 hours while distilling a toluene-methanol azeotrope and was then evaporated to dryness under reduced pressure. The residue was chromatographed over silica gel and elution with an 8-2 methylene chloride-acetone mixture gave 9.2 g of N-(3'-methylcyclohexyl)-3-methoxy-crotonamide whose RMN spectra showed it to be the E isomer.

Analysis: $C_{12}H_{21}NO_2$; molecular weight=211.29 Calculated: %C 68.21; %H 10.02; %N 6.62; Found: 68.2; 10.2; 6.3.

EXAMPLE 10

N-(2'-bornyl)-3-methoxy-crotonamide 16.8 g of diketene were added with stirring to a mixture of 30 g of 2-bornylamine and 200 ml of isopropyl ether and after stirring for 4 hours at 20° C., the mixture was evaporated to dryness under reduced pressure. The residue was chromatographed over silica gel and elution with a 9-1 methylene chloride-acetone mixture gave 39 g of N-(2-bornyl)-acetylacetamide. 30 g of the latter product and 1 g of p-toluene sulfonic acid were added to a mixture of 20 g of methyl orthoformate and 30 ml of methanol and the mixture stood at 20° C. for 16 hours. 2 ml of quinoline were added thereto and the mixture was evaporated to dryness under reduced pressure. The residue was added to toluene and the mixture was heated at 145° C. for 3 hours while distilling a toluene-methanol azeotrope. The mixture was evaporated to dryness under reduced pressure and the residue was chromatographed over silica gel. The product was eluted with an 8-2 methylene chloride-acetone mixture and was crystallized from isopropyl ether to obtain 19 g of N-(2'-bornyl)-3-methoxy-crotonamide melting at 149° C. The RMN spectra showed it was the E somer.

Analysis: $C_{15}H_{25}NO_2$; molecular weight=251.36 Calculated: %C 71.68; %H 10.02; %N 5.57; Found: 71.7; 10.3; 5.3.

EXAMPLE 11

N-(2'-carbethoxy-cyclopentyl)-3-methoxy-crotonamide 4.8 g of diketene were added to a mixture of 9 g of 1-amino-2-carbethoxy-cyclopentane and 90 ml of benzene and after stirring for 72 hours at 20° C., the mixture was evaporated to dryness under reduced pressure. The residue was chromatographed over silica gel and was eluted with an 8-2 methylene chloride-acetone mixture to obtain 7.7 g of N-(2-carbethoxycyclopentyl)-acetylacetamide with a refractive index of $N_D^{22}=1.487$. 6.3 g of the latter product and 0.25 g of p-toluene sulfonic acid were added to a mixture of 4.2 g of methyl orthoformate and 60 ml of methanol and after stirring the mixture at 20° C. for 16 hours, the mixture was evaporated to dryness under reduced pressure. The residue was added to toluene and 0.5 ml of quinoline and the mixture was heated at 145° C. for 1 hour while distilling a toluene-methanol azeotrope. The mixture was evaporated to dryness under reduced pressure and the residue was chromatographed over silica gel. Elution with a 9-1 methylene chloride-acetone mixture gave 1.8 g of N-(2'-carbethoxycyclopentyl)-3-methoxy-crotonamide melting at 74° C. The RMN spectra showed it to be the E isomer.

Analysis: $C_{13}H_{21}NO_4$; molecular weight=255.13 Calculated: %C 61.15; %H 8.29; %N 5.48; Found: 61.4; 8.4; 5.4.

EXAMPLE 12

N-cyclopentyl-3-methoxy-crotonamide 84 g of diketene were added over 10 minutes at 10° C. to a mixture of 85 g of cyclopentylamine and 500 ml of tetrahydrofuran and after stirring the mixture for 6 hours at 20° C., the mixture was evaporated to dryness under reduced pressure. The residue was added to isopropyl ether and was cooled and vacuum filtered to obtain 107 g of N-cyclopentyl-acetylacetamide melting at 52° C. 56 g of the latter product and 1.6 g of p-toluene sulfonic acid were added to a mixture of 40 g of methyl orthoformate and 80 ml of methanol and the mixture was held at 50° C. for 8 hours and 72 hours at 25° C. 4 ml of quinoline were added and the mixture was evaporated to dryness under reduced pressure. The residue was added to toluene and the mixture was heated at 145° C. for 4 hours while distilling a toluene-methanol azeotrope. The mixture was evaporated to dryness under reduced pressure and the residue was chromatographed over silica gel. The product was eluted with an 8-2 methylene chloride-acetone mixture and was crystallized from isopropyl ether to obtain 40 g of N-cyclopentyl-3-methoxy-crotonamide melting at 94° C. The RMN spectra showed the product to be the E isomer.

Analysis: $C_{10}H_{17}NO_2$; molecular weight=183.25 Calculated: %C 65.55; %H 9.35; %N 7.64; Found: 65.7; 9.6; 7.7.

EXAMPLE A

A herbicidal composition was prepared from 250 g of N-cyclooctyl-3-methoxy-crotonamide, 150 g of Ekapersol S (condensation product of sodium naphthalene sulfonate), 5 g of Brecolane NVA (sodium alkylnaphthalene sulfonate), 345 g of Zeosil 39 (precipitated synthetic hydrated silica) and 250 g of Vercoryl S (colloidal Kaolin).

EXAMPLE B

A herbicidal composition was prepared from 400 g of N-(3-cyclohexenyl)-3-methoxy-crotonamide, 84 g of Atlox 4851 (mixture of alkylaryl sulfonate and polyoxyethylene triglyceride with a viscosity of 300 to 700 cps at 25° C.), 56 g of Atlox 4855 (alkylaryl sulfonate mixed with a polyoxyethylene triglyceride with a viscosity of 1500 to 1900 cps at 25° C.), 300 g of xylene and 160 g of cyclohexanone.

HERBICIDAL ACTIVITY

This study was effected with N-(3'-cyclohexenyl)-3-methoxy-crotonamide [compound A], N-cyclooctyl-3-methoxy-crotonamide [compound B], N-cyclohexyl-3-methoxy-crotonamide [compound C], N-cycloheptyl-3-methoxy-crotonamide [compound D], N-(3'-methylcyclohexyl)-3-methoxy-crotonamide [compound E] and N-(2'-carbethoxycyclopentyl)-3-methoxy-crotonamide [compound F].

The plants used were cultivated in a culture flat (23×14×4 cm) with a double bottom with watering from underneath. The species were placed using 20 seeds per species in rows spaced 3 cm apart in a single flat and 4 test were used for each concentration. The growing conditions were as follows: temperature of 20° C.±2° C., about 60% humidity, lighting by fluorescent tubes (day light and bright white) for 6 A.M. to 10 P.M. each day. The dirt mixture was comprised of 10 volumes of regular dirt, 10 volumes of river sand and 2 volumes of peat.

In the pre-emergence test, the treatment was effected on the bottom of the flat before sowing and the first watering was effected by aspersion in a manner to entrain a part of the product to the level of the seeds. In the post-emergence test, the treatment was effected on the above ground part of the plants 15 days after planting. In both cases, the products were applied under standard conditions with a microsprayer at doses of 5, 2.5, 1.25 and 0.625 Kg/ha and at a dilution corresponding to 560 l/ha.

The final readings were made either by weighing or counting the plants 21 days after treatment in the pre and post-emergence tests. The results were expressed as either a percentage of reduction of the weight of the plants P:

$$P = \frac{\text{Weight of control plants} - \text{weight of treated plants}}{\text{Weight of control plants}} \times 100$$

or as a percentage of reduction of the number of plants (percent dead) M;

$$M = \frac{\text{Number of control plants} - \text{number of treated plants}}{\text{Number of control plants}} \times 100$$

The test results are reported in the following tables.

| Pre-Emergence Herbicidal Activity of Compound A | | | | | |
|---|---|---|---|---|---|
| | Doses in Kg/ha | | | | |
| Treated Plants | 5 | 2.5 | 1.25 | 0.625 | |
| Avena Sativa | 100 | 80 | 77 | 0 | M |
| | | 93 | 89 | 66 | P |
| Triticum Sativum | 0 | 0 | 0 | 0 | M |
| | | 52 | 22 | 26 | 0 | P |

(continued)

| Treated Plants | 5 | 2.5 | 1.25 | 0.625 | |
|---|---|---|---|---|---|
| Hordeum Spec. | 46 | 0 | 0 | 0 | M |
|  | 76 | 43 | 37 | 0 | P |
| Zea Mays | 0 | 0 | 0 | 0 | M |
|  | 27 | 0 | 0 | 0 | P |
| Agrostis Tenuis | 100 | 100 | 100 | 86 | M |
|  |  |  |  |  | P |
| Lolium Perenne | 100 | 100 | 100 | 0 | M |
|  |  |  |  | 94 | P |
| Alopecurus Myosuroides | 100 | 100 | 63 | 47 | M |
|  |  |  | 84 | 73 | P |
| Beta Vulgaris | 100 | 100 | 100 | 92 | M |
|  |  |  |  | 99 | P |
| Chenopodium Quinoa | 100 | 100 | 100 | 100 | M |
|  |  |  |  |  | P |
| Chrysanthemum Coronarium | 100 | 100 | 100 | 100 | M |
|  |  |  |  |  | P |
| Sinapis Alba | 100 | 100 | 100 | 100 | M |
|  |  |  |  |  | P |
| Rumex Crispus | 100 | 100 | 35 | 0 | M |
|  |  |  | 95 | 0 | P |
| Trifolium Praetense | 100 | 100 | 100 | 100 | M |
|  |  |  |  |  | P |

Post-Emergence Herbicidal Activity of Compound A

| Treated Plants | 5 | 2.5 | 1.25 | 0.625 | |
|---|---|---|---|---|---|
| Avena Sativa | 100 | 100 | 52 | 0 | M |
|  |  | 87 | 75 |  | P |
| Triticum Sativum | 100 | 0 | 0 | 0 | M |
|  |  | 59 | 31 | 28 | P |
| Hordeum Spec. | 100 | 69 | 0 | 0 | M |
|  | 0 | 92 | 63 | 30 | P |
| Zea Mays | 100 | 35 | 0 | 0 | M |
|  |  | 61 | 41 | 0 | P |
| Agrostis Tenuis | 100 | 100 | 92 | 83 | M |
|  |  |  | 0 | 0 | P |
| Lolium Perenne | 100 | 100 | 66 | 58 | M |
|  |  |  | 81 | 75 | P |
| Alopecurus Myosuroides | 100 | 100 | 100 | 63 | M |
|  |  |  |  | 93 | P |
| Beta Vulgaris | 100 | 100 | 100 | 91 | M |
|  |  |  |  | 93 | P |
| Chenopodium Quinoa | 100 | 100 | 100 | 100 | M |
|  |  |  |  |  | P |
| Chrysanthemum Coronarium | 100 | 100 | 100 | 88 | M |
|  |  |  |  | 95 | P |
| Sinapis Alba | 100 | 100 | 100 | 80 | M |
|  |  |  |  | 86 | P |
| Rumex Crispus | 100 | 100 | 100 | 35 | M |
|  |  |  |  |  | P |
| Trifolium Praetense | 100 | 100 | 100 | 100 | M |
|  |  |  |  |  | P |

Pre-Emergence Herbicidal Activity of Compound B

| Treated Plants | 5 | 2.5 | 1.25 | 0.625 | |
|---|---|---|---|---|---|
| Avena Sativa | 100 | 0 | 0 | 0 | M |
|  | 41 | 54 | 0 |  | P |
| Triticum Sativum | 0 | 0 | 0 | 0 | M |
|  | 51 | 37 | 0 | 0 | P |
| Hordeum Spec. | 0 | 0 | 0 | 0 | M |
|  | 56 | 36 | 0 | 0 | P |
| Zea Mays | 0 | 0 | 0 | 0 | M |
|  | 0 | 0 | 0 | 0 | P |
| Agrostis Tenuis | 100 | 94 | 93 | 0 | M |
|  |  |  |  | 90 | P |
| Lolium Perenne | 100 | 80 | 83 | 65 | M |
|  |  | 95 | 94 | 81 | P |
| Alopecurus Myosuroides | 45 | 47 | 49 | 43 | M |
|  | 83 | 80 | 76 | 58 | P |
| Beta Vulgaris | 100 | 100 | 100 | 92 | M |
|  |  |  |  | 99 | P |
| Chenopodium Quinoa | 100 | 100 | 100 | 100 | M |
|  |  |  |  |  | P |
| Chrysanthemum Coronarium | 100 | 100 | 100 | 100 | M |
|  |  |  |  |  | P |
| Sinapis Alba | 100 | 100 | 100 | 100 | M |
|  |  |  |  |  | P |
| Rumex Crispus | 100 | 100 | 100 | 75 | M |
|  |  |  |  | 93 | P |
| Trifolium Praetense | 100 | 100 | 100 | 100 | M |
|  |  |  |  |  | P |

Post-Emergence Herbicidal Activity of Compound B

| Treated Plants | 5 | 2.5 | 1.25 | 0.625 | |
|---|---|---|---|---|---|
| Avena Sativa | 68 | 0 | 0 | 0 | M |
|  | 92 | 54 | 56 | 42 | P |
| Triticum Sativum | 100 | 0 | 0 | 0 | M |
|  |  | 43 | 28 | 36 | P |
| Hordeum Spec. | 69 | 0 | 0 | 0 | M |
|  | 88 | 25 | 0 | 0 | P |
| Zea Mays | 0 | 0 | 0 | 0 | M |
|  | 0 | 0 | 0 | 0 | P |
| Agrostis Tenuis | 100 | 100 | 100 | 79 | M |
|  |  |  |  | 0 | P |
| Lolium Perenne | 100 | 41 | 0 | 0 | M |
|  |  | 60 | 61 | 58 | P |
| Alopecurus Myosuroides | 100 | 0 | 0 | 0 | M |
|  |  | 42 | 66 | 53 | P |
| Beta Vulgaris | 100 | 100 | 100 | 100 | M |
|  |  |  |  |  | P |
| Chenopodium Quinoa | 100 | 100 | 100 | 100 | M |
|  |  |  |  |  | P |
| Chrysanthemum Coronarium | 100 | 100 | 100 | 100 | M |
|  |  |  |  |  | P |
| Sinapis Alba | 100 | 100 | 100 | 100 | M |
|  |  |  |  |  | P |
| Rumex Crispus | 100 | 100 | 100 | 0 | M |
|  |  |  |  | 0 | P |
| Trifolium Praetense | 100 | 100 | 100 | 100 | M |
|  |  |  |  |  | P |

Pre-Emergence Herbicidal Activity of Compound C

| Treated Plants | 5 | 2.5 | 1.25 | 0.625 | |
|---|---|---|---|---|---|
| Avena Sativa | 100 | 100 | 0 | 0 | M |
|  |  | 71 | 62 |  | P |
| Triticum Sativum | 47 | 0 | 0 | 0 | M |
|  | 69 | 48 | 24 | 0 | P |
| Hordeum Spec. | 29 | 0 | 0 | 0 | M |
|  | 76 | 66 | 42 | 0 | P |
| Zea Mays | 0 | 0 | 0 | 0 | M |
|  | 0 | 0 | 0 | 0 | P |
| Agrostis Tenuis | 100 | 100 | 100 | 94 | M |
|  |  |  |  |  | P |
| Lolium Perenne | 100 | 100 | 93 | 88 | M |
|  |  |  | 95 | 94 | P |
| Alopecurus Myosuroides | 58 | 50 | 0 | 0 | M |
|  | 86 | 84 | 68 | 52 | P |
| Beta Vulgaris | 100 | 100 | 100 | 86 | M |
|  |  |  |  | 94 | P |
| Chenopodium Quinoa | 100 | 100 | 100 | 100 | M |
|  |  |  |  |  | P |
| Chrysanthemum Coronarium | 100 | 100 | 100 | 100 | M |
|  |  |  |  |  | P |
| Sinapis Alba | 100 | 100 | 100 | 100 | M |
|  |  |  |  |  | P |
| Rumex Crispus | 100 | 100 | 100 | 0 | M |
|  |  |  |  | 54 | P |
| Trifolium Praetense | 100 | 100 | 100 | 100 | M |
|  |  |  |  |  | P |
| Galium Aparine | 92 | 67 | 67 | 0 | M |
|  | 95 | 86 | 82 | 44 | P |

Post-Emergence Herbicidal Activity of Compound C

| Treated Plants | 5 | 2.5 | 1.25 | 0.625 | |
|---|---|---|---|---|---|
| Avena Sativa | 100 | 33 | 0 | 0 | M |
|  |  | 77 | 67 | 44 | P |
| Triticum Sativum | 100 | 45 | 0 | 0 | M |
|  |  | 72 | 21 | 0 | P |
| Hordeum Spec. | 100 | 81 | 0 | 0 | M |
|  |  | 96 | 29 | 0 | P |
| Zea Mays | 41 | 0 | 0 | 0 | M |

| Treated Plants | 64 | 0 | 0 | 0 | P |
|---|---|---|---|---|---|
| Agrostis Tenuis | 100 | 100 | 100 | 100 | M |
| | | | | | P |
| Lolium Perenne | 100 | 87 | 42 | 0 | M |
| | | 95 | 67 | 67 | P |
| Alopecurus Myosuroides | 100 | 100 | 0 | 0 | M |
| | | | 73 | 75 | P |
| Beta Vulgaris | 100 | 100 | 100 | 100 | M |
| | | | | | P |
| Chenopodium Quinoa | 100 | 100 | 100 | 100 | M |
| | | | | | P |
| Chrysanthemum Coronarium | 100 | 100 | 100 | 100 | M |
| | | | | | P |
| Sinapis Alba | 100 | 100 | 100 | 100 | M |
| | | | | | P |
| Rumex Crispus | 100 | 100 | 82 | 0 | M |
| | | | 94 | 37 | P |
| Trifolium Praetense | 100 | 100 | 100 | 92 | M |
| | | | | 98 | P |
| Galium Aparine | 100 | 100 | 100 | 100 | M |
| | | | | | P |

Pre-Emergence Herbicidal Activity of Compound D

| Treated Plants | 5 | 2.5 | 1.25 | 0.625 | |
|---|---|---|---|---|---|
| Avena Fatua | 48 | 46 | 0 | 0 | M |
| | 75 | 0 | 0 | 0 | P |
| Triticum Sativum | 51 | 0 | 0 | 0 | M |
| | 77 | 34 | 0 | 0 | P |
| Hordeum Spec. | 40 | 0 | 0 | 0 | M |
| | 87 | 39 | 0 | 0 | P |
| Zea Mays | 0 | 0 | 0 | 0 | M |
| | 0 | 0 | 0 | 0 | P |
| Agrostis Tenuis | 100 | 100 | 100 | 70 | M |
| | | | | 0 | P |
| Lolium Perenne | 100 | 67 | 68 | 39 | M |
| | | 89 | 90 | 75 | P |
| Alopecurus Myosuroides | 38 | 25 | 63 | 0 | M |
| | 0 | 75 | 75 | 63 | P |
| Beta Vulgaris | 100 | 100 | 100 | 100 | M |
| | | | | | P |
| Chenopodium Quinoa | 100 | 100 | 100 | 100 | M |
| | | | | | P |
| Chrysanthemum Coronarium | 100 | 100 | 100 | 100 | M |
| | | | | | P |
| Sinapis Alba | 100 | 100 | 100 | 100 | M |
| | | | | | P |
| Rumex Crispus | 100 | 100 | 100 | 100 | M |
| | | | | | P |
| Trifolium Praetense | 100 | 100 | 100 | 100 | M |
| | | | | | P |
| Galium Aparine | 0 | 45 | 43 | 0 | M |
| | 60 | 0 | 0 | 0 | P |

Post-Emergence Herbicidal Activity of Compound D

| Treated Plants | 5 | 2.5 | 1.25 | 0.625 | |
|---|---|---|---|---|---|
| Avena Fatua | 100 | 100 | 59 | 94 | M |
| | | | 74 | 95 | P |
| Triticum Sativum | 100 | 33 | 0 | 0 | M |
| | | 64 | 0 | 0 | P |
| Hordeum Spec. | 100 | 50 | 0 | 0 | M |
| | | 73 | 25 | 0 | P |
| Zea Mays | 0 | 0 | 0 | 0 | M |
| | 43 | 0 | 0 | 0 | P |
| Agrostis Tenuis | 100 | 100 | 100 | 100 | M |
| | | | | | P |
| Lolium Perenne | 100 | 100 | 100 | 100 | M |
| | | | | | P |
| Alopecurus Myosuroides | 100 | 100 | 100 | 100 | M |
| | | | | | P |
| Beta Vulgaris | 100 | 100 | 100 | 100 | M |
| | | | | | P |
| Chenopodium Quinoa | 100 | 100 | 100 | | M |
| | | | | | P |
| Chrysanthemum Coronarium | 100 | 100 | 100 | 100 | M |
| | | | | | P |
| Sinapis Alba | 100 | 100 | 100 | 100 | M |
| | | | | | P |
| Rumex Crispus | 100 | 100 | 100 | 82 | M |
| | | | | 94 | P |
| Trifolium Praetense | 100 | 100 | 100 | 100 | M |
| | | | | | P |

Pre-Emergence Herbicidal Activity of Compound E

| Treated Plants | 5 | 2.5 | 1.25 | 0.625 | |
|---|---|---|---|---|---|
| Avena Fatua | 100 | 43 | 0 | 0 | M |
| | | 75 | 60 | 52 | P |
| Triticum Sativum | 31 | 0 | 0 | 0 | M |
| | 72 | 58 | 41 | 31 | P |
| Hordeum Spec. | 53 | 0 | 0 | 0 | M |
| | 87 | 59 | 41 | 28 | P |
| Zea Mays | 0 | 0 | 0 | 0 | M |
| | 32 | 0 | 0 | 0 | P |
| Agrostis Tenuis | 100 | 100 | 100 | 100 | M |
| | | | | | P |
| Lolium Perenne | 100 | 100 | 100 | 27 | M |
| | | | | 75 | P |
| Alopecurus Myosuroides | 100 | 67 | 55 | 60 | M |
| | | 86 | 78 | 76 | P |
| Beta Vulgaris | 100 | 100 | 100 | 100 | M |
| | | | | | P |
| Chenopodium Quinoa | 100 | 100 | 100 | 100 | M |
| | | | | | P |
| Chrysanthemum Coronarium | 100 | 100 | 100 | 100 | M |
| | | | | | P |
| Sinapis Alba | 100 | 100 | 100 | 100 | M |
| | | | | | P |
| Rumex Crispus | 100 | 100 | 100 | 100 | M |
| | | | | | P |
| Trifolium Praetense | 100 | 100 | 100 | 100 | M |
| | | | | | P |
| Galium Aparine | 50 | 78 | 67 | 78 | M |
| | 82 | 90 | 78 | 85 | P |

Post-Emergence Herbicidal Activity of Compound E

| Treated Plants | 5 | 2.5 | 1.25 | 0.625 | |
|---|---|---|---|---|---|
| Avena Fatua | 100 | 100 | 50 | 21 | M |
| | | | 74 | 30 | P |
| Triticum Sativum | 100 | 70 | 0 | 0 | M |
| | | 93 | 52 | 23 | P |
| Hordeum Spec. | 100 | 100 | 0 | 0 | M |
| | | | 44 | 0 | P |
| Zea Mays | 70 | 25 | 0 | 0 | M |
| | 85 | 47 | 25 | 0 | P |
| Agrostis Tenuis | 100 | 100 | 100 | 100 | M |
| | | | | | P |
| Lolium Perenne | 100 | 100 | 100 | 100 | M |
| | | | | | P |
| Alopecurus Myosuroides | 100 | 100 | 100 | 50 | M |
| | | | | 58 | P |
| Beta Vulgaris | 100 | 100 | 100 | 100 | M |
| | | | | | P |
| Chenopodium Quinoa | 100 | 100 | 100 | 100 | M |
| | | | | | P |
| Chrysanthemum Coronarium | 100 | 100 | 100 | 100 | M |
| | | | | | P |
| Sinapis Alba | 100 | 100 | 100 | 100 | M |
| | | | | | P |
| Rumex Crispus | 100 | 100 | 100 | 72 | M |
| | | | | 52 | P |
| Trifolium Praetense | 100 | 100 | 100 | 100 | M |
| | | | | | P |
| Galium Aparine | 100 | 100 | 91 | 41 | M |
| | | | 99 | 62 | P |

Post-Emergence Herbicidal Activity of Compound F

| Treated Plants | 5 | 2.5 | 1.25 | 0.625 | |
|---|---|---|---|---|---|
| Avena Fatua | 0 | 0 | 0 | 0 | M |

-continued

| Post-Emergence Herbicidal Activity of Compound F | | | | | |
|---|---|---|---|---|---|
| | Doses in Kg/ha | | | | |
| Treated Plants | 5 | 2.5 | 1.25 | 0.625 | |
| | 0 | 0 | 0 | 0 | P |
| Triticum Sativum | 31 | 0 | 0 | 0 | M |
| | 24 | 0 | 0 | 0 | P |
| Hordeum Spec. | 23 | 0 | 0 | 0 | M |
| | 24 | 0 | 0 | 0 | P |
| Zea Mays | 75 | 60 | 0 | 0 | M |
| | 90 | 66 | 31 | 0 | P |
| Agrostis Tenuis | 0 | 0 | 0 | 0 | M |
| | 27 | 0 | 0 | 0 | P |
| Lolium Perenne | 0 | 0 | 0 | 0 | M |
| | 30 | 0 | 0 | 0 | P |
| Alopecurus Myosuroides | 0 | 0 | 0 | 0 | M |
| | 50 | 50 | 43 | 39 | P |
| Beta Vulgaris | 100 | 100 | 100 | 100 | M |
| | | | | | P |
| Chenopodium Quinoa | 100 | 100 | 100 | 100 | M |
| | | | | | P |
| Chrysanthemum Coronarium | 0 | 0 | 0 | 0 | M |
| | 0 | 0 | 0 | 0 | P |
| Sinapis Alba | 69 | 53 | 0 | 0 | M |
| | 0 | 0 | 0 | 0 | P |
| Rumex Crispus | 100 | 100 | 100 | 100 | M |
| | | | | | P |
| Trifolium Praetense | 100 | 100 | 100 | 100 | M |
| | | | | | P |
| Galium Aparine | 0 | 0 | 0 | 0 | M |
| | 70 | 59 | 62 | 55 | P |

The results in the above Tables show that the tested compounds have interesting herbicidal properties by destroying the majority of the weeds used in the test and showing a greater selectivity to the cereals (wheat, corn, barley, oats) which tolerated the higher doses of the products.

Various modifications of the compositions and methods of the invention may be made without departing from the spirit or scope thereof and it is to be understood that the invention is to be limited only as defined in the appended claims.

We claim:

1. A compound of the formula

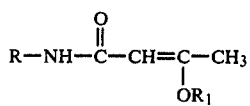

wherein R is selected from the group consisting of adamantyl, bornyl, 5',6'-dihydroendo-5'-dicyclopentadienyl and cycloalkyl of 3 to 8 carbon atoms optionally substituted with a member of the group consisting of alkyl of 1 to 6 carbon atoms, hydroxy and chlorine, cycloalkenyl of 3 to 8 carbon atoms, and $R_1$ is alkyl of 1 to 3 carbon atoms.

2. A compound of claim 1 wherein R is cycloalkyl of 3 to 8 carbon atoms optionally substituted with a member of the group consisting of alkyl of 1 to 6 carbon atoms, hydroxy and chlorine.

3. A compound of claim 1 which is N-cyclohexyl-3-methoxy-crotonamide.

4. A compound of claim 1 which is N-(3'-cyclohexenyl)-3-methoxy-crotonamide.

5. A compound of claim 1 which is N-cyclooctyl-3-methoxy-crotonamide.

6. A compound of claim 1 which is N-(1'-adamantyl)-3-methoxy-crotonamide.

7. A compound of claim 1 which is N-(5',6'-dihydroendo-5'-dicyclopentadienyl)-3-methoxy-crotonamide.

8. A compound of claim 1 which is N-(4'-methylcyclohexyl)-3-methoxy-crotonamide.

9. A compound of claim 1 which is N-cycloheptyl-3-methoxy-crotonamide.

10. A compound of claim 1 which is N-(3'-methylcyclohexyl)-3-methoxy-crotonamide.

11. A compound of claim 1 which is N-(1'-methylcyclohexyl)-3-methoxy-crotonamide.

12. A compound of claim 1 which is N-(2'-bornyl)-3-methoxy-crotonamide.

13. A compound of claim 1 which is N-cyclopentyl-3-methoxy-crotonamide.

14. A herbicidal composition for selectively killing weeds in cultivated cereals comprised of a herbicidally effective amount of a compound of claim 1 and an inert carrier.

15. The composition of claim 14 where R is cycloalkyl of 3 to 8 carbon atoms optionally substituted with a member of the group consisting of alkyl of 1 to 6 carbon atoms, hydroxy and chlorine.

16. A method of killing weeds in cultivated cereals comprising contacting the weeds with an herbicidally effective amount of an active compound of claim 1.

17. The method of claim 16 wherein the active compound is applied pre-emergence.

18. The method of claim 16 wherein the active compound is applied post-emergence.